United States Patent
Anderson et al.

[11] Patent Number: 5,212,171
[45] Date of Patent: May 18, 1993

[54] PESTICIDAL HETEROCYCLIC COMPOUNDS

[75] Inventors: Martin Anderson, Whitstable; Antony G. Brinnand, Selling; Roger E. Woodall, Painters Forstal, all of England

[73] Assignee: Shell Research limited, United Kingdom

[21] Appl. No.: 727,051

[22] Filed: Jul. 9, 1991

[30] Foreign Application Priority Data

Jul. 31, 1990 [GB] United Kingdom ............... 9016799

[51] Int. Cl.$^5$ ................ C07D 319/02; C07D 319/08; A61K 31/335; A01N 43/32
[52] U.S. Cl. ................ 514/230.5; 514/259; 514/452; 549/365; 544/90; 544/283
[58] Field of Search ............ 549/365, 941, 439, 440, 549/15, 19, 32; 514/456, 465, 466, 434, 439, 440, 452, 230.5, 259; 544/90, 283

[56] References Cited

U.S. PATENT DOCUMENTS

| | | | |
|---|---|---|---|
| 4,056,540 | 11/1977 | Buchanan | 549/365 |
| 4,281,012 | 7/1981 | Humbert et al. | 549/365 |
| 4,294,845 | 10/1981 | Humbert et al. | 549/365 |
| 4,611,003 | 9/1986 | Marhold et al. | 514/452 |
| 4,659,736 | 4/1987 | Schlüter et al. | 514/452 |
| 4,691,027 | 9/1987 | Yoshiok et al. | 549/32 |
| 4,876,277 | 10/1989 | Burke et al. | 514/465 |

FOREIGN PATENT DOCUMENTS

23659 1/1990 Japan .
1583274 1/1981 United Kingdom .

Primary Examiner—Mukund J. Shah
Assistant Examiner—Matthew V. Grumbling

[57] ABSTRACT

Compounds of the general formula:

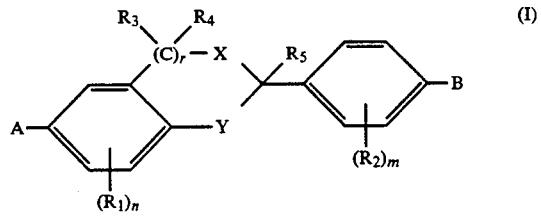

wherein $R_1$ and $R_2$ each independently represents a halogen atom or an alkyl, alkoxy, haloalkyl, haloalkoxy, alkoxycarbonyl, alkenoxy, cyano or nitro group; $R_3$ and $R_4$ each independently represents a hydrogen atom or an alkyl group; $R_5$ represents a hydrogen atom, or an alkyl, alkoxy or alkoxycarbonylalkyl group; X and Y each independently represents an oxygen or sulphur atom or a group N-R, in which R is a hydrogen atom or an alkyl group; n is 0-3; r is 0 or 1; m is 0-4; and A or B represents a group of the general formula:

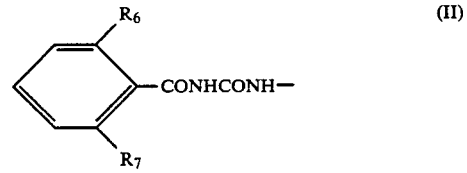

wherein $R_6$ represents a hydrogen or halogen atom, or an alkyl group; and R represents a halogen atom or an alkyl group; the other of A and B being a hydrogen atom or as for $R_1$ or $R_2$, have useful pesticidal activity.

11 Claims, No Drawings

PESTICIDAL HETEROCYCLIC COMPOUNDS

The present invention relates to heterocyclic compounds having pesticidal, especially insecticidal and acaricidal, activity.

The Applicants have discovered a novel class of heterocyclic compounds which have both insecticidal an acaricidal activity.

In accordance with the present invention there is provided a compound of the general formula:

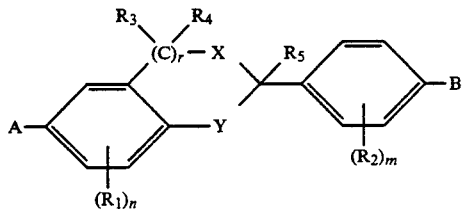

wherein $R_1$ and $R_2$ each independently represents a halogen atom or an alkyl, alkoxy, haloalkyl, haloalkoxy, alkoxycarbonyl, alkenoxy, cyano or nitro group; $R_3$ and $R_4$ each independently represents a hydrogen atom or an alkyl group; $R_5$ represents a hydrogen atom, or an alkyl, alkoxy or alkoxycarbonylalkyl group; X and Y each independently represents an oxygen or sulphur atom or a group N-R, in which R is a hydrogen atom or an alkyl group; n is 0-3; is 0 or 1; m is 0-4; and A or B represents a group of the general formula:

wherein $R_6$ represents a hydrogen or halogen atom, or an alkyl group; and $R_7$ represents a halogen atoms or an alkyl group; the other of A and B being a hydrogen atom or as for $R_1$ or $R_2$.

When n is greater than 1, each $R_1$ may be the same or different, and when m is greater than 1, each $R_2$ may be the same or different.

Preferably, any alkenoxy group, any alkyl group or any alkyl component in any alkoxy, haloalkyl, haloalkoxy or alkoxycarbonyl group has up to 6 carbon atoms.

It is particularly preferred that either (1) $R_2$ represents a halogen atom, or an alkyl, haloalkyl, alkoxy, haloalkoxy or alkenoxy group; $R_3$ and $R_4$ each represents a hydrogen atom; X and Y each independently represents an oxygen or sulphur atom; n is 0; r is 0 or 1; m is 0-2; A represents a group of the general formula II in which $R_6$ and $R_7$ each represents a halogen atom; and B represents a hydrogen or halogen atom or an alkyl, haloalkyl or haloalkoxy group, or (2) $R_3$, $R_4$ and $R_5$ each represents a hydrogen atom; X and Y each represents an oxygen atom; n is 0; r is 1; m is 0; B represents a group of the general formula II in which $R_6$ and $R_7$ each represents a halogen atom; and A represents a halogen atom or an alkyl group.

In case (1), preferably $R_2$ represents a fluorine, chlorine or bromine atom, or a methyl, trifluoromethyl or methoxy group; $R_6$ and $R_7$ each represents a fluorine atom; and B represents a hydrogen, fluorine or chlorine atom or a methyl, trifluoromethyl or trifluoromethoxy group.

In case (2), preferably $R_6$ and $R_7$ each represents a fluorine atom; and A represents a chlorine or bromine atom, or a methyl group.

In accordance with the present invention there is also provided a process for the preparation of a compound of general formula I which comprises hydrogenating a compound of the general formula:

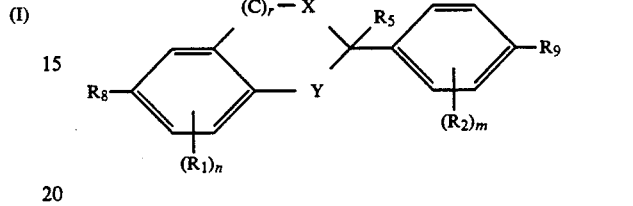

to form a compound of the general formula:

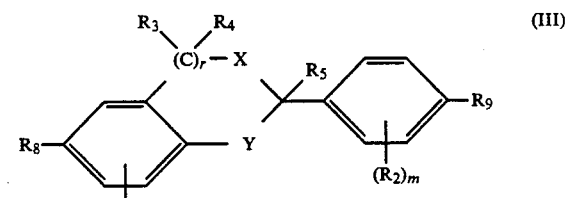

which is reacted with a compound of the general formula:

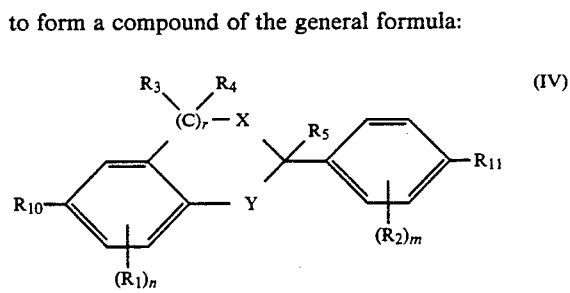

to form a compound of the general formula I, wherein $R_1$, $R_2$, $R_3$, $R_4$, $R_5$, $R_6$, $R_7$, X, Y, n, r and m have the meanings given above; one of $R_8$ and $R_9$ represents a nitro group whilst the other represents a hydrogen or halogen atom or an alkyl, haloalkyl or haloalkoxy group; and one of $R_{10}$ and $R_{11}$ represents an amino group whilst the other represents a hydrogen or halogen atom or an alkyl, haloalkyl or haloalkoxy group.

The hydrogenation of the compound of general formula III is preferably carried out in the presence of a catalyst. Suitable catalysts are platinum or palladium catalysts, particularly a 5% platinum/charcoal catalyst.

The hydrogenation reaction may be carried out in the presence of a solvent or mixture of solvents. Suitable solvents are preferably ethers such as tetrahydrofuran, alcohols such as methanol and ethanol, and hydrocarbons such as toluene. Furthermore, a suitable base may be added as required. Suitable bases are alkali metal carbonates such as anhydrous potassium carbonate.

The reaction is suitably carried out at a temperature in the range 0°-150° C., preferably ambient temperature, and at a pressure of 60 psi or below.

The reaction between compounds of general formulae IV and V is preferably carried out in the presence of a solvent. Suitable solvents are aromatic solvents such as benzene, toluene, xylene or chlorobenzene, hydrocarbons such as petroleum fractions, chlorinated hydrocarbons such as chloroform, methylene chloride or dichloroethane, and ethers such as diethyl ether, dibutyl ether, dioxan and tetrahydrofuran. Mixtures of solvents are also suitable.

Preferably the reaction is carried out at a temperature in the range 0°-110° C., suitably ambient temperature.

Further purification of the product may be achieved by crystallisation from toluene or ethanol, where necessary.

Some compounds of general formula III are themselves novel and constitute a further aspect of the present invention. They may be prepared by reacting a compound of the general formula:

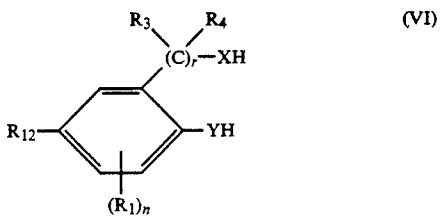

with a compound of the general formula:

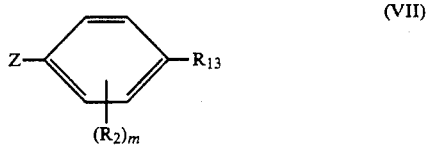

wherein $R_1$, $R_2$, $R_3$, $R_4$, X, Y, n, r and m have the meanings given above; Z represents a group $-CLOR_{14}$ in which $R_{14}$ represents a hydrogen atom or an alkyl or alkoxycarbonylalkyl group, or represents a group C(alkoxy)$_3$; and $R_{12}$ and $R_{13}$ each independently represents a hydrogen or halogen atom or an alkyl, haloalkyl, haloalkoxy or nitro group, with the proviso that no more than one of $R_{12}$ and $R_{13}$ can be a nitro group in any reaction and the proviso that when $R_3$ and $R_4$ each represents a hydrogen atom, $R_{12}$ represents a nitro group, X represents a sulphur atom, Y represents an oxygen atom, n is 0, r is 1 and m is 0, $R_{13}$ cannot be a hydrogen atom, and that when neither of $R_{12}$ and $R_{13}$ is a nitro group, the compound formed is further reacted with nitric acid.

The reaction between compounds of general formulae VI and VII is preferably carried out in the presence of an acid catalyst, which may be any suitable inorganic or organic acid. Suitable acids include sulphonic acids, for example toluene sulphonic acid, carboxylic acids, for example benzoic acid, and mineral acids, for example hydrochloric acid.

The reaction is suitably carried out at a temperature in the range 50°-200° C., particularly 75°-110° C.

The reaction may also be carried out in the presence of a solvent. Suitable solvents include any organic aprotic solvent such as tetrahydrofuran, benzene, hydrocarbons such as toluene, halogenated hydrocarbons, and ethers. Mixed solvents may also be used, such as, for example, toluene with dimethylsulphoxide.

Furthermore, the reaction is suitably carried out under nitrogen, especially when X and/or Y is a sulphur atom.

In the case of further reaction with nitric acid, the temperature of said further reaction is suitably 15°-20° C.

Compounds of general formula I exhibit pesticidal, particularly insecticidal and/or acaricidal, activity. Accordingly the invention also provides a pesticidal composition comprising a compound of general formula I in association with at least one inert carrier therefor. The invention further provides a method of combating pests at a locus, which comprises applying to the locus a pesticidal compound or composition according to the present invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate: and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry-flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing pesticidal, herbicidal, or fungicidal properties. The compounds of the invention are especially useful when applied in admixture with other insecticides, especially organophosphates and pyrethroids. Mixtures with the commercial products fenvalerate, permethrin, cypermethrin, deltamethrin and alphamethrin are especially useful.

The following Examples illustrate the invention; Examples 1 to 77 illustrate the preparation of intermediates of general formula III, while Examples 78 to 155 illustrate the preparation of compounds of general formula I.

EXAMPLE 1

Preparation of 2-(2-fluorophenyl)-6-nitro-1,3-benzodioxan

An intimate mixture of 2-hydroxy-5-nitrobenzyl alcohol (4.56g), 2-fluorobenzaldehyde (4.02g) and benzoic acid (0.2g) was stirred and heated to 90° C. (±5° C.) under nitrogen for 3½ hours. The resulting clear reaction mixture was left to cool for two days whereupon it solidified. This material was dissolved in ethyl acetate (250 ml) and the solution was washed with saturated aqueous sodium bicarbonate, 20% aqueous sodium bisulphite and then with water. The organic phase was dried over sodium sulphate and evaporated to yield the crude product as a solid residue which was purified by suspending briefly in hot ethanol and cooling to 0°–5° C. The pure product was thus obtained as a white crystalline powder (5.3g, 71%), mp 137°–138° C.

EXAMPLES 2 TO 17

By methods analogous to that of Example 1, further compounds of the general formula III were prepared by reaction of compounds of general formula VI with compounds of general formula VII. Details are given in Table I.

TABLE I

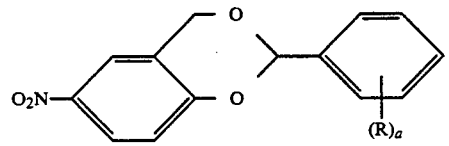

| Example No. | (R)$_a$ | mp °C. | Yield (%) |
|---|---|---|---|
| 2 | 2-Cl | 154–155 | 69 |
| 3 | 4-Cl | 186–187 | 57 |
| 4 | 2,4-Cl$_2$ | 161–162 | 43 |
| 5 | 3,4-Cl$_2$ | 148–149 | 65* |
| 6 | 2,6-Cl$_2$ | 140–141 | 54* |
| 7 | 2-Cl-4-CF$_3$ | 127–129 | 14* |
| 8 | 2,4-F$_2$ | 102–103 | 79 |
| 9 | 2-Br | 149–150 | 78 |
| 10 | 4-CF$_3$ | 116–117 | 40 |
| 11 | 2-CN | 175–176 | 9 |
| 12 | 2-CH$_3$ | 136–137 | 42 |
| 13 | 4-CH$_3$ | 149–150 | 59 |
| 14 | 4-OCF$_3$ | 92–94 | 50 |
| 15 | 2,3-Cl$_2$ | 202–203 | 44 |
| 16 | 2-CF$_3$ | 93–94 | 34 |
| 17 | 2-OCH$_3$ | 159–160 | 36 |

*used without further purification-yield estimated by nmr

EXAMPLE 18

Preparation of 2-[2-chloro-4-(trifluoromethyl)phenyl]-6-nitro-1,3-benzoxathian

A solution of 2-chloro-4-(trifluoromethyl)-benzaldehyde (5.6 g) and 2-mercaptomethyl-4-nitrophenol (2.0 g) in toluene (80 ml) containing a catalytic amount of p-toluenesulphonic acid monohydrate was stirred at reflux temperature for 1 hour in an atmosphere of nitrogen. Water formed in the reaction was removed by means of a Dean-Stark trap. Removal of the solvent under reduced pressure afforded an off-white solid residue which was purified by suspending briefly in hot ethanol (30 ml) and cooling to 0°–5° C. The pure benzoxathian was obtained as colourless crystals (2,97 g, 73%), mp 121°–122° C.

EXAMPLES 19 to 26

By methods analogous to that of Example 18, further compounds of the general formula II were prepared by reaction of compounds of general formula VI with compounds of general formula VII. Details are given in Table II.

TABLE II

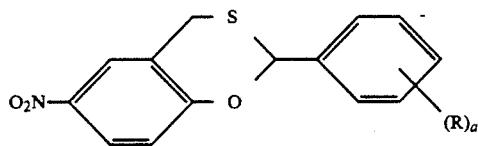

| Example No. | (R)$_a$ | mp °C. | Yield (%) |
| --- | --- | --- | --- |
| 19 | 2-F | 86–87 | 76 |
| 20 | 4-Cl | 145–146 | 68 |
| 21 | 2,4-Cl$_2$ | 97–98 | 60 |
| 22 | 2,6-Cl$_2$ | 149–150 | 57 |
| 23 | 2,4-F$_2$ | 101–102 | 54 |
| 24 | 2-Br | 103–104 | 58 |
| 25 | 4-CH$_3$ | 141–143 | 79 |
| 26 | 2-CF$_3$ | 135–136 | 71 |

EXAMPLE 27

Preparation of 6-bromo-2-(4-nitrophenyl)-1,3-benzodioxan

An intimately ground mixture of 5-bromo-2hydroxybenzyl alcohol (4.06 g), 4-nitrobenzaldehyde (3.93 g) and benzoic acid (0.2 g) was stirred and heated to 85° C. (±5° C.) under nitrogen for 88 hours. The clear melt which formed initially gradually solidified throughout the reaction period. The resulting solidified mass was cooled and dissolved in ethyl acetate (250 ml). The solution was then washed with 20% aqueous sodium carbonate, 20% aqueous sodium bisulphite and finally with brine. After drying over sodium sulphate, the organic phase was evaporated to yield a solid residue which was purified by briefly suspending in hot ethanol (approx. 75 ml) and cooling to 0°–5° C. The pure product was obtained as pale buff-coloured crystals (4.69g, 70%), mp 163°–164° C.

EXAMPLES 28 TO 30

By methods analogous to that of Example 27, further compounds of the general formula III were prepared by reaction of compounds of general formula VI with compounds of general formula VII. Details are given in Table III.

TABLE III

| Example No. | (R)$_a$ | mp °C. | Yield (%) |
| --- | --- | --- | --- |
| 28 | 6-CH$_3$ | 140–141 | 22 |
| 29 | 6-Cl | 144–145 | 51 |
| 30 | 6,8-Cl$_2$ | 169–170 | 39 |

EXAMPLE 31

Preparation of 2-(4-chlorophenyl)-2-methyl-6-nitro-1,3-benzoxathian

A solution of 2-mercaptomethyl-4-nitrophenol (1.0 g) and 4-chloroacetophenone (1.67 g) in toluene (80 ml) containing a catalytic amount of p-toluenesulphonic acid monohydrate (0.1 g) was stirred at reflux temperature for 70 hours in an atmosphere of nitrogen. Water formed in the reaction was removed by means of a Dean-Stark trap. Removal of the solvent under reduced pressure afforded an oily residue which was redissolved in ethyl acetate (200 ml). The solution was washed with 10% (w/v) aqueous sodium carbonate solution and then evaporated under reduced pressure. The resulting residual oil was subjected to flash chromatography on silica gel using methylene chloride as eluant. The crude benzoxathian was thus isolated as an oil which solidified upon trituration with cold ethanol (~5 ml). This material was purified by stirring the suspension at 60° C. for 1 hour and allowing to cool to 0°–5° C. The pure product was obtained as yellow crystals (0.78 g, 45%), mp 163°–164° C.

EXAMPLES 32 TO 33

By a method analogous to that of Example 31, further compounds of the general formula II were prepared by reaction of a compound of general formula VI with a compound of general formula VI. Details are given in Table IV.

TABLE IV

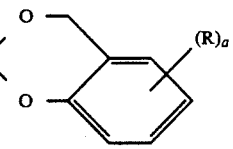

| Example No. | (R)$_a$ | mp °C. | Yield (%) |
| --- | --- | --- | --- |
| 32 | 3,4-Cl$_2$ | resin | 60* |
| 33 | 2,4-F$_2$ | resin | 99* |

*used without further purification-yield estimated by nmr

EXAMPLE 34

Preparation of 2-(2,4-difluorophenyl)-6-nitro-3,1-benzoxathian

A solution of 2-mercapto-5-nitrobenzyl alcohol (2.2 g) and 2,4- difluorobenzaldehyde (3.37 g) in toluene (80 ml) containing a catalytic amount of p-toluenesulphonic acid monohydrate (0.1 g) was heated under reflux for 2 hours in an atmosphere of nitrogen. Water formed in the reaction was removed by means of a Dean-Stark trap. After removal of the solvent under reduced pressure, the remaining residue was redissolved in ethyl acetate. This solution was then washed successively with 10% aqueous sodium carbonate, 10% aqueous sodium bisulphate and brine. After drying over anhydrous sodium sulphate, the solution was evaporated to yield the crude product as a yellow solid. Crystallisation from ethanol afforded the pure benzoxathian as yellow crystals (2.45 g, 67%), mp 119°–120° C.

Examples 35 to 42

By methods analogous to that of Example 34, further compounds of the general formula II were prepared by reaction of compounds of general formula VI with compounds of general formula VII. Details are given in Table V.

TABLE V

O₂N—[benzene ring]—O / S —CH—[benzene ring]—(R)ₐ

| Example No. | (R)ₐ | mp °C. | Yield (%) |
|---|---|---|---|
| 35 | H | 163–165 | 49* |
| 36 | 4-Cl | 149–150 | 48 |
| 37 | 2,4-Cl₂ | 174–175 | 70 |
| 38 | 2,6-Cl₂ | 215–216 | 41 |
| 39 | 2-Br | 134–135 | 33 |
| 40 | 2-CH₃ | 121–122 | 42 |
| 41 | 2-CF₃ | 136–137 | 63 |
| 42 | 2-Cl-4-CF₃ | 151–152 | 40 |

*used without further purification-yield estimated by nmr

EXAMPLE 43

Preparation of 2-(3,4-dichlorophenyl)-2-methyl-6-nitro-3,1-benzoxathian

A solution of 2-mercaptomethyl-4-nitrophenol (1.78 g) and 3,4-dichloroacetophenone (3.83 g) in toluene (80 ml) containing a catalytic amount of p-toluenesulphonic acid monohydrate (0.1 g) was stirred at reflux temperature for 40 hours in an atmosphere of nitrogen. Water formed in the reaction was separated by means of a Dean-Stark trap. Upon cooling to room temperature, some tarry material separated. The supernatant liquor was decanted and washed successively with 10% (w/v) aqueous sodium carbonate solution and brine. After drying over anhydrous sodium sulphate, the solution was evaporated under reduced pressure to leave a mixture of the product and unreacted ketone. This material was subjected to flash chromatography on silica gel using methylene chloride as eluant, whereupon the benzoxathian was isolated as a yellow solid (1.3 g, >95% pure by nmr). Recrystallisation of 0.3 g of this material from ethanol afforded the pure product as yellow crystals (0.27 g), mp 118°–119° C.

EXAMPLES 44 TO 46

By methods analogous to that of Example 43, further compounds of the general formula II were prepared by reaction of compounds of general formula VI with compounds of general formula VII. Details are given in Table VI.

TABLE VI

O₂N—[benzene ring]—O / S —C(CH₃)—[benzene ring]—(R)ₐ

| Example No. | (R)ₐ | mp °C. | Yield (%) |
|---|---|---|---|
| 44 | H | 107–108 | 18 |
| 45 | 4-Cl | 123–124 | 34 |
| 46 | 4-CF₃ | 132–133 | 29 |

EXAMPLE 47

Preparation of 2-(2-fluorophenyl)-5-nitro-1,3-benzodioxole 4-nitrocatechol (3.1 g) and 2-fluorobenzaldehyde (5.0 g) were heated under reflux for 18 hours in toluene (70 ml) containing a catalytic amount (0.2 g) of p-toluenesulphonic acid monohydrate. The water produced in the reaction was separated by means of a Dean-Stark apparatus. The reaction mixture was cooled and some solid material (unreacted catechol) filtered off, washing briefly with methylene chloride. The filtrate was evaporated under reduced pressure and the residue purified by chromatography on silica gel using methylene chloride as eluant. The material thus obtained contained traces of aldehyde which were removed by dissolving in ether and shaking the solution successively with 20% aqueous soldium bisulphite solution, saturated sodium bicarbonate solution and finally with water. The resulting ether solution was dried over anhydrous sodium sulphate and evaporated to yield the pure benzodioxole as pale yellow crystals (4.1 g, 79%), mp 86°–88° C.

EXAMPLES 48 to 57

By methods analogous to that of Example 47, further compounds of the general formula III were prepared by reaction of compounds of general formula VI with compounds of general formula VII. Details are given in Table VII.

TABLE VII

O₂N—[benzene ring]—O / O —CH—[benzene ring]—(R)ₐ

| Example No. | (R)ₐ | mp °C. | Yield (%) |
|---|---|---|---|
| 48 | 2-Cl | 112–114 | 56 |
| 49 | 3-Cl | 80–83 | 61 |
| 50 | 4-Cl | 99–101 | 23* |
| 51 | 2,6-Cl₂ | 120–122 | 27 |
| 52 | 2,4-Cl₂ | resin | 16 |
| 53 | 3,4-Cl₂ | 89–91 | 59 |
| 54 | 2-Br | 134–136 | 70 |
| 55 | 4-CH₃ | 100–102 | 53 |
| 56 | 4-CF₃ | oil | 31 |
| 57 | 2,4-F₂ | 74–76 | 34 |

*used without further purification-yield estimated by nmr

EXAMPLE 58

Preparation of 2-methyl-2-[4-(trifluoromethyl)phenyl]-5-nitro-1,3-benzodioxole (i) A solution of catechol (5.5 g) and 4-(trifluoromethyl)acetophenone (10.3 g) in toluene (150 ml) containing a catalytic amount (0.2 g) of p-toluenesulphonic acid monohydrate was heated under reflux for 3 days. Water produced in the condensation was separated by means of a Dean-Stark trap. After removal of the solvent under reduced pressure, the residue was purified by chromatography on silica gel using methylene chloride as eluant. Pure 2-methyl-2-[4-(trifluoromethyl)phenyl]-1,3-benzodioxole was obtained as a colourless oil (10.8 g, 77%).

(ii) A solution of 2-methyl-2-[4-(trifluoromethyl)-phenyl]-1,3-benzodioxole (5.6g) in dichloroethane (15 ml) was added over 10 minutes to vigorously stirred nitric acid (50% w/v, 25 ml) keeping the temperature at 15°-20° C. by means of a cooling bath. The resulting reaction mixture was stirred for a further 1 hour at 20° C., poured into water (200 ml) and extracted with methylene chloride (3×100 ml). After drying over anhydrous sodium sulphate, the extract was evaporated under reduced pressure. The residue was purified by chromatography on silica gel using methylene chloride as eluant, affording the pure product benzodioxole as a pale yellow oil (5.3 g, 82%).

EXAMPLES 59 TO 62

By methods analogous to that of Example 58, further compounds of the general formula II were prepared by reaction of compounds of general formula VI with compounds of general formula VII. Details are given in Table VIII.

TABLE VIII

| Example No. | $(R)_a$ | R | mp °C. | Yield (%) |
|---|---|---|---|---|
| 59 | 4-Cl | $CH_3$ | oil | 83 |
| 60 | 3,4-$Cl_2$ | $CH_3$ | oil | 81 |
| 61 | 2,4-$F_2$ | $CH_3$ | 85-87 | 95 |
| 62 | H | $CH_2CO_2C_2H_5$ | oil | 37 |

EXAMPLE 63

Preparation of 2-ethoxy-2-phenyl-5-nitro-1,3-1-benzodioxole

A solution of 4-nitrocatechol (3.1 g) and triethyl orthobenzoate (6.7 g) in dry toluene (40 ml) was heated under reflux for 2½ hours. The solvent was then removed under reduced pressure and the resulting residue pruified by chromatography on silica gel using methylene chloride as eluant. The pure benzodioxole was obtained as a pale yellow oil (3.8 g, 66%).

EXAMPLE 64

Preparation of 2-(2,4-dichlorophenyl)5-nitro-1,3-benzoxathiole

2-Mercapto-4-nitrophenol (2.0 g) and 2,4-dichlorobenzaldehyde (2.0 g) were heated under reflux for 6 hours in toluene (70 ml) containing a catalytic amount (0.2 g) of p-toluenesulphonic acid monohydrate. Water formed in the reaction was separated by means of a Dean-Stark apparatus. The resulting reaction mixture was evaporated under reduced pressure, and the residue extracted with cyclohexane. The cyclohexane solution was then evaporated and the residue chromatographed on silica gel using methylene chloride/5% (v/v) methanol as eluant. The material obtained at this stage was contaminated with unreacted aldehyde. This was removed by stirring a methylene chloride solution of the crude product with 30% aqueous sodium bisulphite for 2 hours and then washing the solution successively with saturated sodium bicarbonate solution and water. After drying over anhydrous sodium sulphate, the methylene chloride was removed under reduced pressure. Crystallisation of the residue afforded the pure product as pale yellow crystals (0.7 g, 21%), mp 106°-108° C.

EXAMPLES 65 TO 72

By methods analogous to that of Example 64, further compounds of the general formula II were prepared by reaction of compounds of general formula VI with compounds of general formula VII. Details are given in Table IX.

TABLE IX

| Example No. | $(R)_a$ | mp °C. | Yield (%) |
|---|---|---|---|
| 65 | 2-F | 99-101 | 47 |
| 66 | 4-Cl | oil | 58* |
| 67 | 3,4-$Cl_2$ | 112-114 | 40 |
| 68 | 2-Cl-4-$CF_3$ | oil | 21* |
| 69 | 2,4-$F_2$ | 75-77 | 88 |
| 70 | 2-Br | 163-165 | 51 |
| 71 | 4-$CF_3$ | oil | 37* |
| 72 | 2-$CF_3$ | oil | 34* |

*used without further purification-yield estimated by nmr

EXAMPLE 73

Preparation of 2-(4-chlorophenyl)-2-methyl-5-nitro-1,3-benzoxathiole

A solution of 2-mercapto-4-nitrophenol (1.7 g) and 4-chloroacetophenone (3.1 g) in toluene (75 ml) containing acatalytic amount of p-toluenesulphonic acid monohydrate (0.2 g) was heated under reflux for 6 hours, removing water formed in the reaction by means of a Dean-Stark trap. The reaction mixture was evaporated under reduced pressure and the resulting residue was purified by chromatography on silica gel using methylene chloride as eluant. The pure benzoxathiole was obtained as pale yellow crystals (15. g, 49%), mp 87°-° C.

EXAMPLES 74 to 77

By methods analogous to that of Example 73, further compounds of the general formula II were prepared by reaction of compounds of general formula VI with compounds of general formula VII. Details are given in Table X.

TABLE X

| Example No. | $(R)_a$ | mp °C. | Yield (%) |
|---|---|---|---|
| 74 | 3,4-$Cl_2$ | oil | 64* |
| 75 | 2,4-$Cl_2$ | oil | 21* |
| 76 | 2,4-$F_2$ | oil | 26* |
| 77 | 4-$CF_3$ | oil | 53* |

*used without further purification-yield estimated by nmr

Elemental analysis data for the intermediates of general formula III described above, where measured, is set out in Table XI below.

TABLE XI

| Example | C | | H | | N | |
|---|---|---|---|---|---|---|
| No. | Calc. | Found | Calc. | Found | Calc. | Found |
| 1 | 61.1 | 60.9 | 3.7 | 3.6 | 5.1 | 5.0 |
| 2 | 57.7 | 57.3 | 3.5 | 3.4 | 4.8 | 4.6 |
| 3 | 57.7 | 57.8 | 3.5 | 3.6 | 4.8 | 5.0 |
| 4 | 51.6 | 51.6 | 2.8 | 3.0 | 4.3 | 4.9 |
| 8 | 57.4 | 56.6 | 3.1 | 3.2 | 4.8 | 4.6 |
| 9 | 50.0 | 50.0 | 3.0 | 2.9 | 4.2 | 3.9 |
| 10 | 55.4 | 55.8 | 3.1 | 3.2 | 4.3 | 4.5 |
| 11 | 63.8 | 63.8 | 3.6 | 3.5 | 9.9 | 9.8 |
| 12 | 66.4 | 65.5 | 4.8 | 4.6 | 5.2 | 5.0 |
| 13 | 66.4 | 66.5 | 4.8 | 4.9 | 5.2 | 5.1 |
| 14 | 52.8 | 53.2 | 3.0 | 3.2 | 4.1 | 4.6 |
| 15 | 51.6 | 51.6 | 2.8 | 3.0 | 4.3 | 4.9 |
| 16 | 55.4 | 55.9 | 3.1 | 3.3 | 4.3 | 4.6 |
| 17 | 62.7 | 62.9 | 4.6 | 4.5 | 4.9 | 5.0 |
| 18 | 48.0 | 47.5 | 2.4 | 2.6 | 3.7 | 3.7 |
| 19 | 57.7 | 58.3 | 3.5 | 3.7 | 4.8 | 4.9 |
| 20 | 54.6 | 54.3 | 3.3 | 3.3 | 4.6 | 4.6 |
| 21 | 49.1 | 49.1 | 2.7 | 2.8 | 4.1 | 4.1 |
| 22 | 49.1 | 48.9 | 2.7 | 2.7 | 4.1 | 4.0 |
| 23 | 54.4 | 54.7 | 2.9 | 3.0 | 4.5 | 4.6 |
| 24 | 47.7 | 47.2 | 2.9 | 3.0 | 4.0 | 3.9 |
| 25 | 62.7 | 62.3 | 4.6 | 4.5 | 4.9 | 4.9 |
| 26 | 52.8 | 52.2 | 3.0 | 3.1 | 4.1 | 3.9 |
| 27 | 50.0 | 49.8 | 3.0 | 3.0 | 4.2 | 4.4 |
| 28 | 66.4 | 66.4 | 4.8 | 5.1 | 5.2 | 5.2 |
| 29 | 57.7 | 57.2 | 3.5 | 3.6 | 4.8 | 5.2 |
| 30 | 51.6 | 51.6 | 2.8 | 2.6 | 4.3 | 4.4 |
| 31 | 56.0 | 56.3 | 3.8 | 4.0 | 4.4 | 4.3 |
| 34 | 54.4 | 54.8 | 2.9 | 3.3 | 4.5 | 4.7 |
| 36 | 54.6 | 54.6 | 3.3 | 3.5 | 4.6 | 4.6 |
| 37 | 49.1 | 49.3 | 2.7 | 3.0 | 4.1 | 4.2 |
| 38 | 49.1 | 49.5 | 2.7 | 2.8 | 4.0 | 4.3 |
| 39 | 47.7 | 48.0 | 2.9 | 3.0 | 4.0 | 4.0 |
| 40 | 62.7 | 62.3 | 4.6 | 4.5 | 4.9 | 4.9 |
| 41 | 52.8 | 52.8 | 3.0 | 3.1 | 4.1 | 4.2 |
| 42 | 48.0 | 48.4 | 2.4 | 2.7 | 3.7 | 3.9 |
| 43 | 50.6 | 50.4 | 3.1 | 3.4 | 3.9 | 4.1 |
| 44 | 62.7 | 62.2 | 4.6 | 4.5 | 4.9 | 4.8 |
| 45 | 56.0 | 55.9 | 3.8 | 3.8 | 4.4 | 4.3 |
| 46 | 54.1 | 53.8 | 3.4 | 3.5 | 3.9 | 3.9 |
| 47 | 59.8 | 59.4 | 3.1 | 3.4 | 5.4 | 5.6 |
| 48 | 56.2 | 56.5 | 2.9 | 3.4 | 5.0 | 5.3 |
| 49 | 56.2 | 56.3 | 2.9 | 2.9 | 5.0 | 5.0 |
| 51 | 50.0 | 49.6 | 2.2 | 2.0 | 4.5 | 4.1 |
| 52 | 50.0 | 50.1 | 2.2 | 2.5 | 4.5 | 4.7 |
| 53 | 50.0 | 49.8 | 2.2 | 2.9 | 4.5 | 5.0 |
| 54 | 48.4 | 48.2 | 2.5 | 2.3 | 4.3 | 4.2 |

TABLE XI-continued

| Example | C | | H | | N | |
|---|---|---|---|---|---|---|
| No. | Calc. | Found | Calc. | Found | Calc. | Found |
| 55 | 65.4 | 65.3 | 4.3 | 4.6 | 5.4 | 5.6 |
| 56 | 54.0 | 54.2 | 2.6 | 2.8 | 4.5 | 4.2 |
| 57 | 55.9 | 56.2 | 2.5 | 2.6 | 5.0 | 5.1 |
| 58 | 55.4 | 55.7 | 3.1 | 3.3 | 4.3 | 4.5 |
| 59 | 57.6 | 57.5 | 3.4 | 3.6 | 5.0 | 4.8 |
| 60 | 51.5 | 51.4 | 2.8 | 2.9 | 4.3 | 4.3 |
| 61 | 57.3 | 57.8 | 3.1 | 3.3 | 4.8 | 4.8 |
| 62 | 62.0 | 61.9 | 4.6 | 4.6 | 4.0 | 4.1 |
| 63 | 62.7 | 63.3 | 4.5 | 4.6 | 4.9 | 4.8 |
| 64 | 47.6 | 47.9 | 2.1 | 2.6 | 4.3 | 4.7 |
| 65 | 56.3 | 56.8 | 2.9 | 2.2 | 5.1 | 5.0 |
| 67 | 47.6 | 47.4 | 2.1 | 2.3 | 4.3 | 4.4 |
| 69 | 52.9 | 52.7 | 2.4 | 2.7 | 4.7 | 4.6 |
| 70 | 46.1 | 45.9 | 2.4 | 2.3 | 4.1 | 4.1 |
| 73 | 54.6 | 54.9 | 3.3 | 3.4 | 4.6 | 4.5 |

EXAMPLE 78

Preparation of 2,6-difluoro-N-[[[2-(2-fluorophenyl)-1,3-benzodioxan-6-yl]amino]carbonyl]benzamide A suspension of 2-(2-fluorophenyl)-6-nitro-1,3-benzodioxan (2.0 g) in ehtanol 250 ml) was hydrogenated at ≦60 psi hydrogen pressure in the presence of 5% platinum/charcoal (0.3 g) and anhydrous potassium carbonate (0.2 g) at ambient temperature. The resulting reaction mixture was filtered and evaporated under reduced pressure to afford the crude aniline derivative which was dried azeotropically by dissolving in toluene and evaporation under reduced pressure. The dried material was redissolved in dry toluene (20 ml) and treated with 2,6-difluorobenzoyl isocyanate (1.4 g), briefly brought to reflux temeprature and left to cool overnight. After cooling to 0°–5° C., the precipitate of product was separated, washed with cold toluene followed by light petroleum and dried under reduced pressure at approx. 60° C. The pure product was thus obtained as a white microcrystalline powder (2.7 g, 87%), mp 203°–206° C.

EXAMPLES 79 TO 120

By methods analogous to that of Example 78, further compounds of the general formula I were prepared from intermediates of the general formula III. Details are given in Tables XII to XVI.

TABLE XII

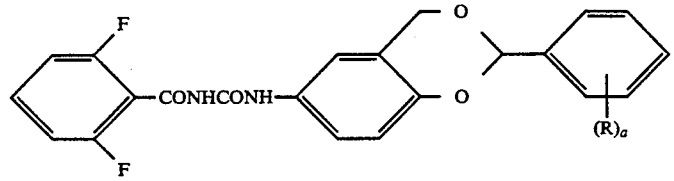

| Example No. | (R)$_a$ | mp °C. | Yield (%) |
|---|---|---|---|
| 79 | H | 188–190 | 63 |
| 80 | 2-Cl | 202–205 | 85 |
| 81 | 4-Cl | 225–230 | 50 |
| 82 | 2,4-Cl$_2$ | 214–215 | 50 |
| 83 | 3,4-Cl$_2$ | 200–203 | 73 |
| 84 | 2,6-Cl$_2$ | 203–204 | 68 |
| 85 | 2-Cl-4-CF$_3$ | 219–220 | 43 |
| 86 | 2,4-F$_2$ | 220–221 | 57 |
| 87 | 2-Br | 208–210 | 79 |
| 88 | 4-CF$_3$ | 235–236 | 64 |
| 89 | 2-CH$_3$ | 198–200 | 42 |
| 90 | 4-CH$_3$ | 209–211 | 67 |
| 91 | 4-OCF$_3$ | 221–223 | 72 |

TABLE XII-continued
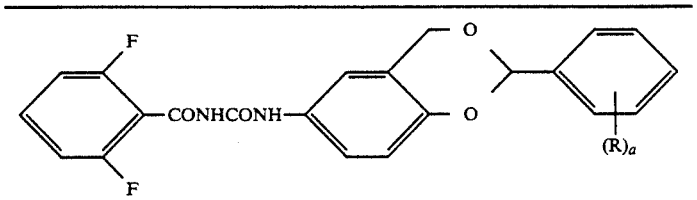
| Example No. | (R)$_a$ | mp °C. | Yield (%) |
|---|---|---|---|
| 92 | 2,3-Cl$_2$ | 221–222 | 64 |
| 93 | 2-CF$_3$ | 201–202 | 55 |
| 94 | 2-OCH$_3$ | 205–206 | 72 |
TABLE XIII
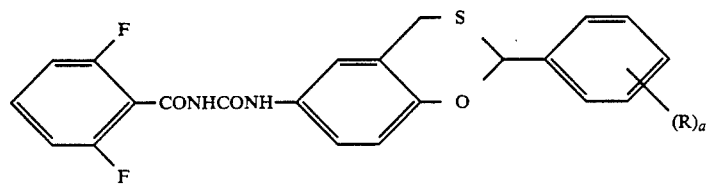
| Example No. | (R)$_a$ | mp °C. | Yield (%) |
|---|---|---|---|
| 95 | 2-Cl-4-CF$_3$ | 215–216 | 91 |
| 96 | 2-F | 222–224 | 82 |
| 97 | 4-Cl | 209–210 | 80 |
| 98 | 2,4-Cl$_2$ | 217–218 | 81 |
| 99 | 2,6-Cl$_2$ | 229–231 | 79 |
| 100 | 2,4-F$_2$ | 228–229 | 80 |
| 101 | 2-Br | 223–224 | 77 |
| 102 | 4-CH$_3$ | 215–216 | 55 |
| 103 | 2-CF$_3$ | 225–226 | 89 |
| 104 | H | 194–195 | 74 |
TABLE XIV
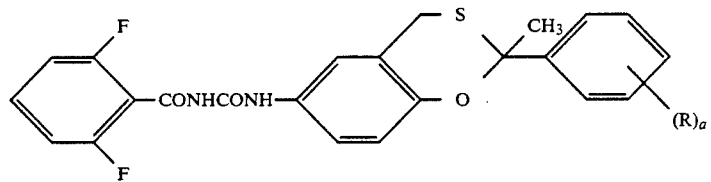
| Example No. | (R)$_a$ | mp °C. | Yield (%) |
|---|---|---|---|
| 105 | 4-Cl | 201–202 | 66 |
| 106 | 3,4-Cl$_2$ | 194–195 | 32 |
| 107 | 2,4-F$_2$ | 161–163 | 79 |
TABLE XV
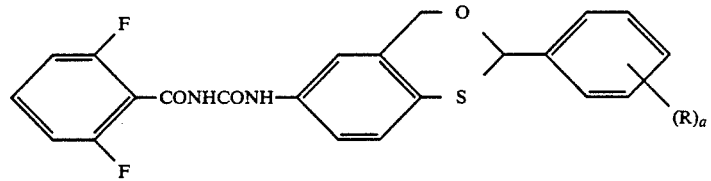
| Example No. | (R)$_a$ | mp °C. | Yield (%) |
|---|---|---|---|
| 108 | 2,4-F$_2$ | 242–244 | 79 |
| 109 | H | 221–222 | 78 |
| 110 | 4-Cl | 231–233 | 79 |
| 111 | 2,4-Cl$_2$ | 222–224 | 55 |
| 112 | 2-CF$_3$ | 213–215 | 25 |
| 113 | 2,6-Cl$_2$ | 225–226 | 32 |
| 114 | 2-Cl-4-CF$_3$ | 210–211 | 66 |
| 115 | 2-Br | 215–216 | 71 |

TABLE XV-continued

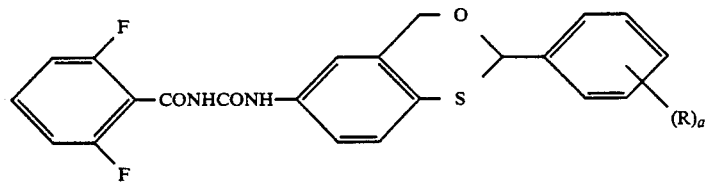

| Example No. | (R)$_a$ | mp °C. | Yield (%) |
|---|---|---|---|
| 116 | 2-CH$_3$ | 205–206 | 75 |

TABLE XVI

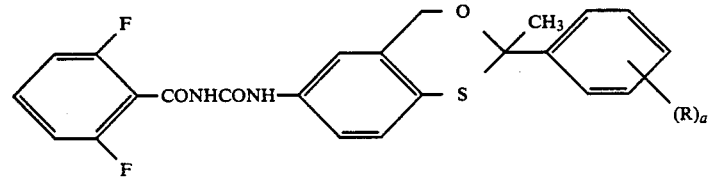

| Example No. | (R)$_a$ | mp °C. | Yield (%) |
|---|---|---|---|
| 117 | H | 203–205 | 61 |
| 118 | 4-Cl | 237–238 | 85 |
| 119 | 3,4-Cl$_2$ | 224–225 | 66 |
| 120 | 4-CF$_3$ | 243–244 | 47 |

EXAMPLE 121

Preparation of N-[[[4-(6-bromo-1,3-benzodioxan-2-yl)-phenyl[amino[carbonyl[-2,6-difluorobenzamide A suspension of 6-bromo-2-(4-nitrophenyl)-1,3-benzodioxan (2.05 g) in toluene (150 ml) was hydrogenated at ≦60 psi hydrogen pressure in the presence of 5% platinum/charcoal (0.5 g) and anhydrous potassium carbonate (0.5 g) at ambient temperature. The reaction mixture was filtered and evaporated under reduced pressure, azeotropically removing the water formed in the reaction. The resulting crude aniline derivative was redissolved in dry toluene (25 ml) and treated with 2.6-difluorobenzoyl isocyanate (1.2 g), warming briefly to approx. 60° C. then allowing the stirred reaction mixture to cool overnight. Cooling to 0°–5° C. afforded a precipitate of impure product which was purified by crystallisation from ethanol (0.52 g, 17%), mp 194°–95° C.

EXAMPLES 122 TO 123

By methods analogous to that of Example 121, further compounds of the general formula I were prepared from intermediates of the general formula III. Details are given in Table XVII.

EXAMPLE 124

Preparation of 2,6-difluoro-N-[[[2-(2-fluorophenyl)-1,3-benzodioxol-5-yl]amino]carbonyl]benzamide A solution of 2-(2-fluorophenyl)5-nitro-1,3-benzodioxole (2.6 g) in ethanol (150 ml) was hydrogenated at ≦60 psi hydrogen pressure in the presence of 5% platinum/charcoal (0.2 g) and anhydrous potassium carbonate (0.2 g) at ambient temperature. The resulting reaction mixture was filtered through 'Hiflo supercel' (BDH) and the filtrate evaporated under reduced pressure. The residue was dried azeotropically by redissolving in toluene (120 ml) and evaporating under reduced pressure. The crude aniline thus obtained was redissolved in dry toluene (30 ml) and treated with 2,6-difluorobenzoyl isocyanate (2.0 g) at reflux temperature for 1 hour. The acylurea crystallised out on cooling and was filtered off, washing with cold toluene. This material was further purified by chromatography on silica gel, eluting with methylene chloride containing 5% (v/v) methanol. Additional product was recovered from the toluene filtrate by chromatorgraphy using the same system. The pure acylurea was obtained as colourless crystals (total yield 3.2 g, 77%), mp 189°–192° C.

TABLE XVII

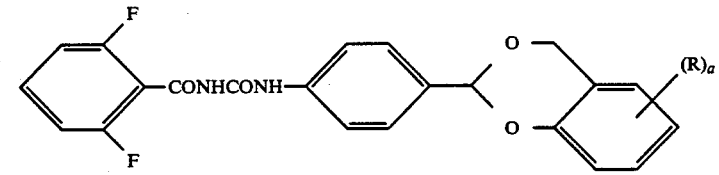

| Example No. | (R)$_a$ | mp °C. | Yield (%) |
|---|---|---|---|
| 122 | 6-CH$_3$ | 185–186 | 32 |
| 123 | 6-Cl | 185–186 | 14 |

EXAMPLES 125 TO 141

By methods analogous to that of Example 124, further compounds of the general formula I were prepared from intermediates of the general formula III. Details are given in Table XVIII.

TABLE XVIII

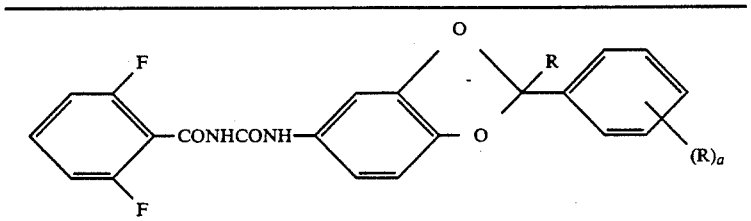

| Example No. | (R)$_a$ | R | mp °C. | Yield (%) |
|---|---|---|---|---|
| 125 | H | H | 198–200 | 88 |
| 126 | 2-Cl | H | 234–236 | 71 |
| 127 | 3-Cl | H | 200–201 | 68 |
| 128 | 4-Cl | H | 207–209 | 54 |
| 129 | 2,6-Cl$_2$ | H | 240–243 | 67 |
| 130 | 2,4-Cl$_2$ | H | 211–212 | 47 |
| 131 | 3,4-Cl$_2$ | H | 228–230 | 62 |
| 132 | 2-Br | H | 225–228 | 55 |
| 133 | 4-CH$_3$ | H | 171–173 | 77 |
| 134 | 4-CF$_3$ | H | 191–193 | 78 |
| 135 | 2,4-F$_2$ | H | 202–203 | 56 |
| 136 | 4-CF$_3$ | CH$_3$ | 156–157 | 61 |
| 137 | 4-Cl | CH$_3$ | 102–104 | 81 |
| 138 | 3,4-Cl$_2$ | CH$_3$ | 155–156 | 61 |
| 139 | 2,4-F$_2$ | CH$_3$ | 138–140 | 85 |
| 140 | H | CH$_2$CO$_2$C$_2$H$_5$ | 121–122 | 73 |
| 141 | H | OC$_2$H$_5$ | 237–239 | 61 |

EXAMPLE 142

Preparation of N-[[[2-(2,4-dichlorophenyl)-1,3-benzoxathiol-5-yl]amino]carbonyl]-2,6-difluorobenzamide A solution of 2-(2,4-dichlorophenyl)-5-nitro-1,3-benzoxathiole (0.7 g) in ethanol (100 ml) was hydrogenated at ≦60 psi hydrogen pressure in the presence of 5% platinum/charcoal (0.2 g) and anhydrous potassium carbonate (0.2 g). The resulting reaction mixture was filtered through 'Hiflo supercel' (BDH) and evaporated under reduced pressure. Traces of ethanol and water were removed by redissolving the residue in toluene and evaporating under reduced pressure. The crude aniline thus obtained was then dissolved in dry toluene (70 ml) and treated with 2,6-difluorobenzoyl isocyanate (0.4 g) at reflux temperature for 45 minutes. The product was isolated by removing the solvent under reduced pressure and purifying the residue by chromatography on silica gel using methylene chloride/5% (v/v) methanol as eluant. The pure acylurea was obtained as colourless crystals (0.3 g, 31%), mp 206°–208° C.

EXAMPLES 143 TO 155

By methods analogous to that of Example 142, further compound of the general formula I were prepared from intermediates of the general formula III. Details are given in Table XIX.

TABLE XIX

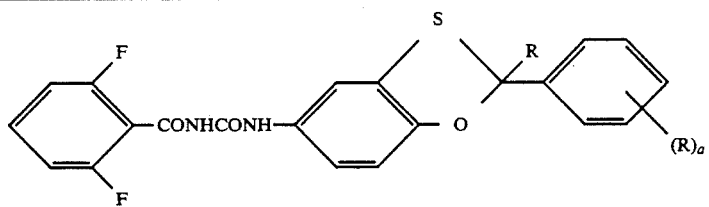

| Example No. | (R)$_a$ | R | mp °C. | Yield (%) |
|---|---|---|---|---|
| 143 | 2-F | H | 204–206 | 86 |
| 144 | 4-Cl | H | 196–198 | 27 |
| 145 | 3,4-Cl$_2$ | H | 219–221 | 57 |
| 146 | 2-Cl-4-CF$_3$ | H | 168–170 | 36 |
| 147 | 2,4-F$_2$ | H | 209–211 | 71 |
| 148 | 2-Br | H | 180–181 | 46 |
| 149 | 4-CF$_3$ | H | 235–237 | 31 |
| 150 | 2-CF$_3$ | H | 166–168 | 49 |
| 151 | 4-Cl | CH$_3$ | 130–132 | 84 |
| 152 | 3,4-Cl$_2$ | CH$_3$ | 180–182 | 45 |
| 153 | 4-CF$_3$ | CH$_3$ | 173–175 | 45 |
| 154 | 2,4-Cl$_2$ | CH$_3$ | 203–205 | 51 |
| 155 | 2,4-F$_2$ | CH$_3$ | 207–209 | 43 |

Elemental analysis data for the compounds of general formula I described above is set out in Table II below.

TABLE XX

| Example No. | Analysis (%) | | | | | |
|---|---|---|---|---|---|---|
| | C | | H | | N | |
| | Calc. | Found | Calc. | Found | Calc. | Found |
| 78 | 61.7 | 60.2 | 3.5 | 3.3 | 6.5 | 6.3 |
| 79 | 64.4 | 64.2 | 3.9 | 4.1 | 6.8 | 7.1 |
| 80 | 59.4 | 60.5 | 3.4 | 3.5 | 6.3 | 5.8 |
| 81 | 59.4 | 59.2 | 3.4 | 3.4 | 6.3 | 6.2 |
| 82 | 55.1 | 55.3 | 2.9 | 3.3 | 5.8 | 6.2 |
| 83 | 55.1 | 55.0 | 2.9 | 3.2 | 5.8 | 5.7 |
| 84 | 55.1 | 55.4 | 2.9 | 2.7 | 5.8 | 5.3 |
| 85 | 53.9 | 53.7 | 2.7 | 2.8 | 5.5 | 5.8 |
| 86 | 59.2 | 60.0 | 3.2 | 2.9 | 6.3 | 7.5 |
| 87 | 54.0 | 53.0 | 3.1 | 3.1 | 5.7 | 6.6 |
| 88 | 57.7 | 56.9 | 3.2 | 3.4 | 5.9 | 6.2 |
| 89 | 65.1 | 65.1 | 4.3 | 4.5 | 6.6 | 7.4 |
| 90 | 65.1 | 62.9 | 4.3 | 4.4 | 6.6 | 6.6 |
| 91 | 55.9 | 56.8 | 3.1 | 3.1 | 5.7 | 5.6 |
| 92 | 55.1 | 55.2 | 2.9 | 3.0 | 5.9 | 6.1 |
| 93 | 57.8 | 58.0 | 3.2 | 3.5 | 5.9 | 6.0 |
| 94 | 62.7 | 62.8 | 4.1 | 4.3 | 6.4 | 6.4 |
| 95 | 52.2 | 52.3 | 2.7 | 3.0 | 5.3 | 5.2 |
| 96 | 59.5 | 59.5 | 3.4 | 3.6 | 6.3 | 6.4 |
| 97 | 57.3 | 57.1 | 3.3 | 3.5 | 6.1 | 6.0 |
| 98 | 53.4 | 53.3 | 2.9 | 3.1 | 5.7 | 5.6 |
| 99 | 53.4 | 53.3 | 2.9 | 3.0 | 5.7 | 5.7 |
| 100 | 57.1 | 56.8 | 3.1 | 3.4 | 6.1 | 6.0 |
| 101 | 52.3 | 52.3 | 3.0 | 3.2 | 5.5 | 5.7 |
| 102 | 62.7 | 62.7 | 4.1 | 4.3 | 6.4 | 6.4 |
| 103 | 55.9 | 56.1 | 3.1 | 3.2 | 5.7 | 5.6 |
| 104 | 62.0 | 61.8 | 3.8 | 3.8 | 6.6 | 6.6 |
| 105 | 58.2 | 58.1 | 3.6 | 3.9 | 5.9 | 5.8 |
| 106 | 54.2 | 54.4 | 3.2 | 3.3 | 5.5 | 5.6 |
| 107 | 58.0 | 57.9 | 3.4 | 3.6 | 5.9 | 5.9 |
| 108 | 57.1 | 56.9 | 3.1 | 3.3 | 6.1 | 6.0 |
| 109 | 62.0 | 62.2 | 3.8 | 3.9 | 6.6 | 6.6 |
| 110 | 57.3 | 57.3 | 3.3 | 3.4 | 6.1 | 6.0 |
| 111 | 53.4 | 53.4 | 2.9 | 3.1 | 5.7 | 5.3 |
| 112 | 55.9 | 55.7 | 3.1 | 3.3 | 5.8 | 5.6 |
| 113 | 53.4 | 53.4 | 2.9 | 3.0 | 5.7 | 5.7 |
| 114 | 52.2 | 52.1 | 2.7 | 2.8 | 5.3 | 5.3 |
| 115 | 52.3 | 52.4 | 3.0 | 3.0 | 5.3 | 5.6 |
| 116 | 62.7 | 62.6 | 4.1 | 4.1 | 6.4 | 6.4 |
| 117 | 62.7 | 62.7 | 4.1 | 4.1 | 6.4 | 6.4 |
| 118 | 58.2 | 58.5 | 3.6 | 3.5 | 5.9 | 5.9 |
| 119 | 54.2 | 54.4 | 3.7 | 3.4 | 5.5 | 5.4 |
| 120 | 56.7 | 56.9 | 3.4 | 3.5 | 5.5 | 5.5 |
| 121 | 54.0 | 55.4 | 3.1 | 3.2 | 5.7 | 5.7 |
| 122 | 65.1 | 65.2 | 4.3 | 4.3 | 6.6 | 6.7 |
| 123 | 59.4 | 59.8 | 3.4 | 3.8 | 6.3 | 6.2 |
| 124 | 60.9 | 61.1 | 3.1 | 3.0 | 6.8 | 7.0 |
| 125 | 63.6 | 63.4 | 3.5 | 3.7 | 7.1 | 7.2 |
| 126 | 58.5 | 57.7 | 3.0 | 3.4 | 6.5 | 6.7 |
| 127 | 58.5 | 58.4 | 3.0 | 3.1 | 6.5 | 6.4 |
| 128 | 58.5 | 58.5 | 3.0 | 3.4 | 6.5 | 6.9 |
| 129 | 54.2 | 53.9 | 2.6 | 2.5 | 6.0 | 6.0 |
| 130 | 54.2 | 54.5 | 2.6 | 2.8 | 6.0 | 6.1 |
| 131 | 54.2 | 54.8 | 2.6 | 3.0 | 6.0 | 6.2 |
| 132 | 53.1 | 52.9 | 2.7 | 2.8 | 5.9 | 5.8 |
| 133 | 64.4 | 64.3 | 3.9 | 3.9 | 6.8 | 6.7 |
| 134 | 56.9 | 56.9 | 2.8 | 2.6 | 6.0 | 5.8 |
| 135 | 58.4 | 58.9 | 2.8 | 3.1 | 6.5 | 6.5 |
| 136 | 57.7 | 57.9 | 3.1 | 3.5 | 5.9 | 5.8 |
| 137 | 59.4 | 59.2 | 3.4 | 3.6 | 6.3 | 6.2 |
| 138 | 55.1 | 55.6 | 2.9 | 3.1 | 5.9 | 5.9 |
| 139 | 59.8 | 60.1 | 3.1 | 3.6 | 6.3 | 6.3 |
| 140 | 62.2 | 61.9 | 4.1 | 4.4 | 5.8 | 5.8 |
| 141 | 62.7 | 62.9 | 4.1 | 4.1 | 6.4 | 6.3 |
| 142 | 52.4 | 52.1 | 2.5 | 2.7 | 5.8 | 5.6 |
| 143 | 58.6 | 58.5 | 3.0 | 3.3 | 6.5 | 6.4 |
| 144 | 56.4 | 56.1 | 2.9 | 3.2 | 6.3 | 6.1 |
| 145 | 52.5 | 53.0 | 2.5 | 2.9 | 5.8 | 5.6 |
| 146 | 51.3 | 51.5 | 2.3 | 2.5 | 5.5 | 5.5 |
| 147 | 56.3 | 55.9 | 2.7 | 3.1 | 6.2 | 6.1 |
| 148 | 51.3 | 51.0 | 2.7 | 2.7 | 5.7 | 5.6 |
| 149 | 55.0 | 54.5 | 2.7 | 3.0 | 5.8 | 5.8 |
| 150 | 55.0 | 54.6 | 2.7 | 2.9 | 5.8 | 5.8 |
| 151 | 57.3 | 56.8 | 3.3 | 3.7 | 6.1 | 5.8 |

TABLE XX-continued

| Example No. | Analysis (%) | | | | | |
|---|---|---|---|---|---|---|
| | C | | H | | N | |
| | Calc. | Found | Calc. | Found | Calc. | Found |
| 152 | 53.3 | 53.5 | 2.8 | 3.0 | 5.7 | 5.7 |
| 153 | 55.9 | 55.7 | 3.0 | 3.2 | 5.7 | 5.6 |
| 154 | 53.3 | 53.6 | 2.8 | 3.1 | 5.7 | 5.4 |
| 155 | 57.1 | 57.4 | 3.0 | 3.0 | 6.1 | 6.1 |

EXAMPLE 156

Insecticidal Activity

Insecticidal activity of compounds of general formula I was assessed against the following pests:
Spodoptera littoralis (Egyptian cotton leafworm)
Aedes aegypti (yellow fever mosquito)
Trialeurodes vaporariorum (greenhouse whitefly)

The test methods employed for each species appear below. In each test, unless otherwise stated, solutions or suspensions of test compound were made up over a range of concentrations in water (initially 0.1% w) containing 10%w acetone and 0.025% w "TRITON X-100" (trade mark) surface active agent (the condensation product of ethylene oxide with an alkyl phenol). These solutions were sprayed at a rate equivalent to 340 liters per hectare ($3.4 \times 10^{-5} m^3/m^2$) onto Petri dishes containing either test species per se or diet onto which test species were subsequently introduced, as indicated. In some assays leaf discs infested with test species were sprayed whilst other assays involved the spraying of plants which were infested subsequently with test species after the spray solution had dried. The tests were all conducted under normal insectary conditions (23° C.±2° C., fluctuating humidity and light).

Mortality assessments were made as indicated below, in terms of percentage mortality figures. In each test a $LC_{50}$ (the dosage of active material required to kill half of the test species) for the compound was calculated from the mortality figures and compared with the corresponding $LC_{50}$ for a standard insecticide, ethyl parathion, in the same test. The results are expressed as toxicity indices thus:

$$\text{toxicity index} = \frac{LC_{50} \text{ (parathion)}}{LC_{50} \text{ (test compound)}} \times 100$$

(i) Spodoptera littoralis (7 day)(Sl 7D)
Test solutions were sprayed as indicated above onto Petri dishes containing a nutritious diet for Egyptian cotton leafworm larvae. When the spray deposit had dried, each dish was infested with ten 2nd instar larvae. Mortality assessments were made 7 days after spraying.

(ii) Aedes aegypti (Aa)
Early 4th instar larvae were used. Test solutions were made up to 0.5 ppm of test compound (and progressive half-dilutions) in water containing 0.04% w "TRITON X-100" (trade mark); acetone was initially present to aid solution, but was allowed to evaporate off before introduction of larvae. Ten early 4th instar larvae were placed in 100 ml of test solution held at 28° C., and after 48 hours, larval mortality was recorded. The final mortality was assessed by counting the number of emerged adult mosquitoes after one week.

(iii) Trialeurodes vaporariorum (Tv)

French bean plants (*Phaseolus vulgaris*) with two fully expanded leaves were placed in a breeding culture of *T.vaporariorum*, also on French bean plants, which were then disturbed to ensure resettlement on the introduced plants. During the subsequent 24 hour period, eggs were deposited and kept at 27° C., with 14 hours photoperiod. All adult whiteflies were then carefully removed, leaving egg samples of a known age. After eight days the majority of eggs had hatched. Leaf discs containing the newly hatched nymphs were then cut from the leaves and transferred to moist filter paper. The discs were examined under a low-powered microscope to determine the exact number of 1st instar nymphs per disc and to remove any unhatched eggs. On average, 70-100 nymphs were found per disc. The discs were transferred into Petri dishes and sprayed with test solutions as described above. After 6 days percentage mortalities were assessed.

TABLE XXI

| Compound of Example No. | Insecticidal Activity Toxicity Index | | |
|---|---|---|---|
| | S.l. | A.a. | T.v. |
| 78 | 550 | 890 | 230 |
| 79 | 1100 | 2 | 4000 |
| 80 | 30 | 450 | B |
| 81 | 1200 | 900 | B |
| 82 | 1000 | 620 | 2800 |
| 83 | 530 | | B |
| 84 | 420 | 180 | B |
| 85 | 1400 | 210 | |
| 86 | 2100 | 300 | 560 |
| 87 | 150 | 1200 | B |
| 88 | 560 | 71 | B |
| 89 | 26 | 890 | 320 |
| 90 | 680 | 3 | 130 |
| 91 | 570 | 80 | B |
| 92 | 80 | 212 | |
| 93 | 4200 | 268 | 3300 |
| 94 | 18 | 3 | |
| 95 | 220 | 46 | 1800 |
| 96 | 300 | 170 | B |
| 97 | 190 | 13 | |
| 98 | 410 | 57 | B |
| 99 | 60 | 46 | B |
| 100 | 280 | 120 | B |
| 101 | 60 | 90 | 570 |
| 102 | 35 | 23 | B |
| 103 | 320 | 41 | B |
| 104 | 100 | 31 | B |
| 105 | 150 | 5 | 160 |
| 106 | 490 | 14 | |
| 108 | A | | |
| 109 | 320 | 140 | |
| 110 | 34 | 58 | |
| 111 | 210 | 190 | |
| 112 | 160 | 230 | B |
| 113 | A | A | B |
| 114 | 310 | A | |
| 115 | 32 | A | A |
| 116 | 180 | 150 | B |
| 121 | 49 | 130 | |
| 122 | 17 | | |
| 123 | 130 | 21 | |
| 124 | 100 | 150 | 1000 |
| 125 | 310 | 120 | B |
| 126 | 94 | 540 | B |
| 127 | 450 | 240 | B |
| 128 | 1800 | 630 | B |
| 129 | 17 | | |
| 130 | 3370 | 790 | 1530 |
| 131 | 3000 | 190 | |
| 132 | 90 | 490 | |
| 133 | | 19 | |
| 134 | 3500 | 130 | |
| 135 | 790 | 620 | B |
| 136 | 18000 | 1300 | 2300 |

TABLE XXI-continued

| Compound of Example No. | Insecticidal Activity Toxicity Index | | |
|---|---|---|---|
| | S.l. | A.a. | T.v. |
| 137 | 5700 | 1100 | 3200 |
| 138 | 12000 | 1200 | 1700 |
| 139 | 6000 | 17 | 1200 |
| 140 | 130 | 9 | B |
| 141 | 1700 | 280 | |
| 142 | 1000 | 200 | 2600 |
| 143 | 110 | 120 | B |
| 144 | 460 | 18 | 330 |
| 145 | 600 | 18 | |
| 146 | 1500 | 330 | 30 |
| 147 | 200 | 83 | 2100 |
| 148 | 420 | 400 | 1400 |
| 149 | 420 | 23 | |
| 150 | 360 | 1300 | 9 |
| 151 | 430 | 53 | 500 |
| 152 | 100 | 43 | B |
| 153 | 700 | | 2500 |
| 154 | 1100 | 190 | |
| 155 | 400 | 170 | |

Grades A and B indicate mortalities of 70-100% and 40-69%, respectively, at the initial test concentration of 0.1% w (1000 ppm).

EXAMPLE 157

Acaricidal Activity (mite life cycle)

Acaricidal activity of some compounds of formula I was assessed, employing adult female glasshouse red spider mites, *Tetranychus urticae* (T.u.), by the following procedure.

2 cm diameter leaf discs cut from the leaves of French bean plants were placed, underside uppermost, on 5.5 cm diameter filter papers, kept moist by a cotton wool wick dipped in water.

Each leaf disc was infested with 25 to 30 adult female mites which were removed after 6 hours, leaving bout 50 eggs on each disc. Within 5 days the eggs hatched. The freshly emerged larvae on the leaf discs were sprayed with solutions of test compound made up as in Example 156 above, at a rate equivalent to 340 liters per hectare ($3.4 \times 10^{-5}$ m$^3$/m$^2$).

The discs were thereafter kept under normal laboratory conditions (23° C.±2° C., fluctuating humidity and 16 hours day length). After 7 days assessment was made of the number of mites emerging as adults.

From the results the $LC_{50}$ was calculated, as given in Table XXII below.

TABLE XXII

| Compound of Example No. | Acaricidal Activity $LC_{50}$ (% active ingredient in spray) |
|---|---|
| 82 | 0.00023 |
| 84 | 0.00036 |
| 85 | 0.00031 |
| 87 | 0.0029 |
| 92 | 0.085 |
| 93 | 0.00022 |
| 134 | 0.09 |
| 142 | 0.0015 |
| 145 | 0.053 |
| 147 | 0.05 |

We claim:

1. A compound of the general formula:

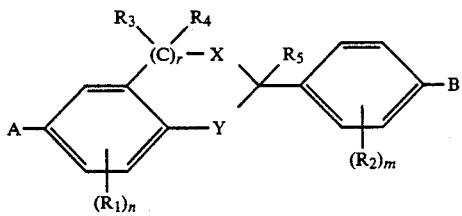

(I)

wherein $R_1$ and $R_2$ each independently represents a halogen atom or an alkyl, alkoxy, haloalkyl, haloalkoxy, alkoxycarbonyl, alkenoxy, cyano or nitro group; $R_3$ and $R_4$ each independently represents a hydrogen atom or an alkyl group; $R_5$ represents a hydrogen atom, or an alkyl, alkoxy or alkoxycarbonylalkyl group; X and Y each independently represents an oxygen atom or a group N-R, in which R is a hydrogen tom or an alkyl group; n is 0-3; r is 1; m is 0-4; and A or B represents a group of the general formula:

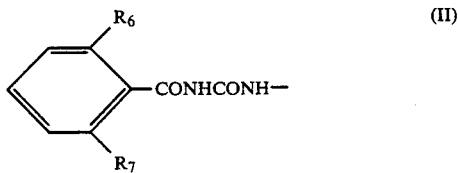

(II)

wherein $R_6$ represents a hydrogen or halogen atom, or an alkyl group; and $R_7$ represents a halogen atom or an alkyl group; the other of A and B being a hydrogen atom or as for $R_1$ or $R_2$.

2. A compound as claimed in claim 1 wherein any alkenoxy group, any alkyl group or any alkyl component in any alkoxy, haloalkyl, haloalkoxy or alkoxycarbonyl group has up to 6 carbon atoms.

3. A compound as claimed in claim 2 wherein $R_2$ represents a halogen atom, or an alkyl, haloalkyl, alkoxy, haloalkoxy or alkenoxy group; $R_3$ and $R_4$ each represents a hydrogen atom; X and Y each independently represents an oxygen atom; n is 0; r is 1; m is 0-2; A represents a group of the general formula II in which $R_6$ and $R_7$ each represents a halogen atom; and B represents a hydrogen or halogen atom or an alkyl, haloalkyl or haloalkoxy group.

4. A compound as claimed in claim 2 wherein $R_3$, $R_4$ and $R_5$ each represents a hydrogen atom; X and Y each represents an oxygen atom; n is 0; r is 1; m is 0; B represents a group of the general formula II in which $R_6$ and $R_7$ each represents a halogen atom; and A represents a halogen atom or an alkyl group.

5. A compound as claimed in claim 3 wherein $R_2$ represents a fluorine, chlorine or bromine atom, or a methyl, trifluoromethyl or methoxy group; $R_6$ and $R_7$ each represents a fluorine atom; and B represents a hydrogen, fluorine or chlorine atom or a methyl, trifluoromethyl or trifluoromethoxy group.

6. A compound as claimed in claim 4 wherein $R_6$ and $R_7$ each represents a fluorine atom; and A represents a chlorine or bromine atom or a methyl group.

7. A pesticidal composition comprising a compound as claimed in claim 1 together with a carrier.

8. A composition as claimed in claim 7, which comprises at least two carrier, at least one of which is a surface-active agent.

9. A method of combating pests at a locus, which comprises applying to the locus an effective amount of a compound as claimed in claim 1.

10. A compound as claimed in claim 1, wherein $R_3$, $R_4$ and $R_5$ are hydrogen; X and Y are oxygen; n is 0; m is 1 or 2; $R_2$ is chlorine or trifluoromethyl; B is hydrogen, chlorine or trifluoromethyl; and A is a group of formula (II), where $R_6$ and $R_7$ are both fluorine.

11. A method of combating pests at a locus, which comprises applying to the locus an effective amount of a composition as claimed in claim 7.

* * * * *

UNITED STATES PATENT AND TRADEMARK OFFICE
CERTIFICATE OF CORRECTION

PATENT NO. : 5,212,171

DATED : May 18, 1993

INVENTOR(S) : MARTIN ANDERSON ET AL.

It is certified that error appears in the above-identified patent and that said Letters Patent is hereby corrected as shown below:

Column 26, line 27:
Claim 8, line 2 of the claim, "carrier" should read --carriers--.

In the Abstract, after the first formula, "ps" should be deleted; and third line from the bottom, "R" should read "$R_7$".

Signed and Sealed this

Eighth Day of February, 1994

*Attest:*

BRUCE LEHMAN

*Attesting Officer*     *Commissioner of Patents and Trademarks*